United States Patent [19]

Hirose et al.

US005504235A

[11] Patent Number: 5,504,235
[45] Date of Patent: Apr. 2, 1996

[54] METHOD FOR DECOMPOSING POLYSILOXANE

[75] Inventors: Toshifumi Hirose; Ryotaro Tsuji; Katsuya Ouchi, all of Hyogo, Japan

[73] Assignee: Kanegafuchi Chemical Industry Co., Ltd., Osaka, Japan

[21] Appl. No.: 479,194

[22] Filed: Jun. 7, 1995

[30] Foreign Application Priority Data

Jun. 15, 1994 [JP] Japan .................................. 6-155433
Aug. 26, 1994 [JP] Japan .................................. 6-224033
Sep. 19, 1994 [JP] Japan .................................. 6-248300

[51] Int. Cl.$^6$ .................................. C07F 7/08; C07F 7/18
[52] U.S. Cl. ............... 556/467; 252/182.23; 252/182.28; 252/183.11
[58] Field of Search ....................... 556/467; 252/182.23, 252/182.28, 183.11

[56] References Cited

U.S. PATENT DOCUMENTS

| | | | |
|---|---|---|---|
| 2,698,861 | 1/1955 | Shorr ......................................... | 556/467 |
| 4,202,831 | 5/1980 | Schlak et al. ............................ | 556/467 |
| 5,183,914 | 2/1993 | Yeh et al. ................................. | 556/467 |
| 5,258,537 | 11/1993 | Takeuchi et al. ......................... | 556/467 |
| 5,391,797 | 2/1995 | Hirose et al. ............................ | 556/467 |

FOREIGN PATENT DOCUMENTS

| | | |
|---|---|---|
| 0618211 | 10/1994 | European Pat. Off. . |
| 2418249 | 9/1979 | France . |
| 2015550 | 9/1979 | United Kingdom . |

OTHER PUBLICATIONS

Database WPI, Week 8404, Derwent Publications Ltd., London, GB; SU–A–1 004 391 (Chernyshev E A) 15 Mar. 1983 (Abstract).
Database WPI, Week 8927, Derwent Publications, Ltd., London, GB: JP–A–1 132 590 (Toshiba Silicone KK) 25 May 1989 (Abstract).

*Primary Examiner*—Paul F. Shaver
*Attorney, Agent, or Firm*—Foley & Lardner

[57] ABSTRACT

When a polysiloxane or siloxane is contacted with a mixture which comprises an orthoester, a compound having an active hydrogen-containing group and an acid catalyst, it is easily decomposed even at room temperature to provide a silicon compound having a lower molecular weight such as an alkoxysilane.

17 Claims, No Drawings

METHOD FOR DECOMPOSING POLYSILOXANE

BACKGROUND OF THE INVENTION

1. Field of the Invention

The present invention relates to the decomposition of a polysiloxane to a silicon compound having a lower molecular weight.

Further, the present invention relates to a method for producing an alkoxysilane which is one of important intermediates used in a silicone industry.

2. Description of the Related Art

Since a polysiloxane is a chemically stable compound, it should be treated at high temperature optionally in the presence of an alkali or an acid to decompose it.

A synthesis reaction of an alkoxysilane compound using a decomposition reaction of a polysiloxane is known, but a yield is low. That is, Japanese Patent KOKAI Publication No. 132590/1989 discloses a process for producing an alkoxysilane of the formula:

wherein $R^2$ is an alkyl group, $R^3$ is a substituted or unsubstituted monovalent hydrocarbon group, b is 1, 2 or 3, and c is 0, 1 or 2 comprising reacting an alkoxysilane of the formula:

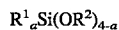

wherein $R^2$ is the same as defined above, $R^1$ is a substituted or unsubstituted monovalent hydrocarbon group, and a is 0, 1, 2 or 3 with a polysiloxane in the presence of a titanium compound catalyst.

According to this process, for example, tetramethoxysilane and a polymethylhydrogensiloxane of the formula:

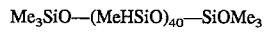

are reacted to obtain dimethoxymethylsilane. Further, tetraethoxysilane and octamethylcyclotetrasiloxane of the formula:

are reacted to obtain diethoxydimethylsilane.

It is assumed that, in this process, the desired alkoxysilane would be synthesized through cleavage of a Si—O bond of the polysiloxane by the titanium compound used as the catalyst and an insertion reaction of the alkoxy group from the raw material alkoxysilane between the cleaved bond (depolymerization reaction).

While this process has advantages that hydrogen chloride or chlorosilane is not by-produced because it is a halogen-free reaction, it has disadvantages that a yield of the desired product is decreased because of many side reactions, the process requires a troublesome fractionating step, and a large amount of by-produced polysiloxane remains as a residue.

SUMMARY OF THE INVENTION

One object of the present invention is to provide a method for decomposing a polysiloxane under mild conditions.

Another object is to provide a method for decomposing a polysiloxane, so that a silicone rubber is reutilized, a polysiloxane film is removed from a substrate, or a silicone surface is modified by partial decomposition thereof.

A further object of the present invention is to provide a method for synthesizing an alkoxysilane compound in a high yield by the use of a decomposition reaction of a polysiloxane, which method is accompanied with fewer side reactions.

A yet further object of the present invention is to provide a composition for decomposing a polysiloxane.

According to a first aspect of the present invention, there is provided a method for decomposing a polysiloxane comprising contacting a polysiloxane with a mixture which comprises an orthoester, a compound having an active hydrogen-containing group and an acid catalyst.

According to a second aspect of the present invention, there is provided a composition for decomposing a polysiloxane comprising an orthoester, a compound having an active hydrogen-containing group and an acid catalyst.

According to a third aspect of the present invention, there is provided a method for producing an alkoxysilane comprising reacting an orthoester with a compound selected from the group consisting of siloxanes and polysiloxanes, in the presence of a compound having an active hydrogen-containing group and an acid catalyst.

DETAILED DESCRIPTION OF THE INVENTION

In the present invention, examples of the orthoester to be used are orthoformates (e.g. methyl orthoformate, ethyl orthoformate, propyl orthoformate, butyl orthoformate, octyl orthoformate, etc.), orthoacetates (e.g. methyl orthoacetate, ethyl orthoacetate, propyl orthoacetate, butyl orthoacetate, octyl orthoacetate, etc.), methyl orthobenzoate, and so on.

Among them, methyl orthoesters such as methyl orthoformate and methyl orthoacetate are preferred in view of their reactivity.

An amount of the orthoester depends on the object of the decomposition. When it is intended to proceed the decomposition largely, the orthoester is used in an amount of at least 0.5 mole, preferably at least 1.0 mole per one mole of the Si—O—Si bond of the polysiloxane. An upper limit of the amount of the orthoester is not limited. Usually, the upper limit is 20 moles, preferably 10 moles per one mole of the Si—O—Si bond of the polysiloxane.

The siloxane or polysiloxane to be used in the present invention is a compound comprising at least two silicon atoms which are bonded through an oxygen atom.

Specific examples of the siloxane or polysiloxane are silicone oils, silicone raw rubbers, vulcanized silicone rubbers, silicone varnishes, silicone resins, polysilsesquioxane, and so on.

Examples of a substituent group on the silicon atoms are a hydrogen atom, an alkyl group having 1 to 12 carbon atoms, a substituted alkyl group having 1 to 12 carbon atoms such as a chloromethyl group, an alkenyl group having 2 to 12 carbon atoms such as a vinyl group and an allyl group, an aryl group having 6 to 12 carbon atoms such as a phenyl group and a tolyl group, an alkoxy group having 1 to 12 carbon atoms such as a methoxy group and an ethoxy group, and the like.

Among the siloxanes and polysiloxanes, those having a Si—H bonds are preferred since they react quickly.

The present invention is particularly useful, when preparation of an alkoxysilane having a Si—H bond in the molecule is intended. In this case, a polysiloxane having Si—H bonds in a molecule is used as a raw material.

The polysiloxane may be a straight one, a branched one or cyclic one, or a mixture thereof. In such polysiloxane, examples of an organic group to be bonded to the silicon atoms are an alkyl group having 1 to 12 carbon atoms, a substituted alkyl group having 1 to 12 carbon atoms such as a chloromethyl group, an alkenyl group having 2 to 12 carbon atoms such as a vinyl group and an allyl group, an aryl group having 6 to 12 carbon atoms such as a phenyl group and a tolyl group.

Specific examples of the polysiloxane are a linear polysiloxane of the formula:

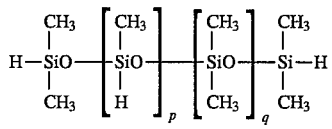

wherein p and q are each 0 or an integer up to 3000, a linear polysiloxane of the formula:

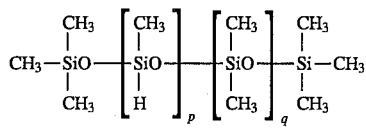

wherein p and q are each 0 or an integer up to 3000, and a cyclic polysiloxane of the formula:

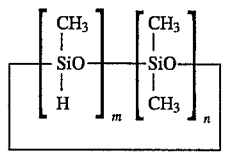

wherein m and n are each 0 or an integer up to 100, provided that a sum of m and n (m+n) is at least 2.

A content of the Si—H bonds in the polysiloxane is not critical. As the content of the Si—H bonds increases, the yield of the intended alkoxysilane increases.

Other examples of the polysiloxane are

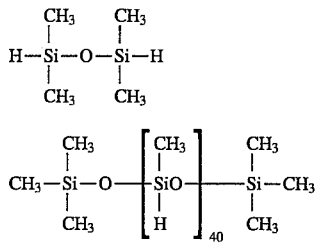

a branched polymethylhydrogensiloxane comprising units of the formula: $(CH_3)_2HSi_{0.5}$ and units of the formula: $SiO_2$ and having a hydrogen content of 1.03 wt. % and a viscosity at 25° C. of 24 cSt, and a cyclic polysiloxane of the formula:

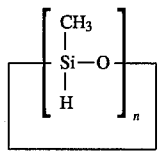

wherein n is an integer of 2 to 100.

In the present invention, a polysiloxane having no Si—H bond may be used. Examples of such polysiloxane are

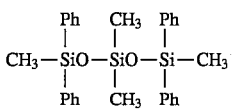

wherein Ph represents a phenyl group, and

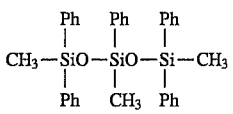

wherein Ph represents a phenyl group.

The compound having the active hydrogen-containing group herein used is a compound which generates an alcohol when it is reacted with the orthoester, or a compound having a hydroxyl group, a carboxyl group, a mercapto group, an amino group, and so on in a molecule such as water, an alcohol, a carboxylic acid, a mercaptan, an amine and the like.

Among them, water, an alcohol and a carboxylic acid are preferred.

Examples of the alcohol are monohydric alcohols such as methanol, ethanol, isopropanol, n-propanol, n-butanol, etc, and polyhydric alcohols such as ethylene glycol, propylene glycol, glycerol, etc. Among them, methanol and ethanol are preferred, and methanol is particularly preferred.

Examples of the carboxylic acid are formic acid, acetic acid, propionic acid, acrylic acid, and so on.

In the present invention, the use of the compound having the active hydrogen-containing group is essential. When this compound is not used, the reaction does not proceed, or if it proceeds, a reaction rate is very low. The reaction rate increases in proportion to the amount of the compound having the active hydrogen-containing group.

In the present invention, the compound having the active hydrogen-containing group is not necessarily used in a stoichiometric amount. This is one of the characteristics of the present invention.

That is, the amount of the compound having the active hydrogen-containing group can be an amount sufficient for initiating the reaction. When it is used in a molar amount of only one tenth of the mole of the silicon atoms of the polysiloxane or the orthoester molecules, the reaction can be initiated at room temperature, and the desired alkoxysilane is obtained quantitatively.

Accordingly, it is very easy to recover the desired alkoxysilane with high purity from the reaction mixture, for example, by distillation.

As the catalyst, an acid is preferred. Examples of the acid catalyst are inorganic acids such as sulfuric acid, p-toluenesulfonic acid, hydrochloric acid, phosphoric acid, etc., organic acids such as acetic acid, etc., and Lewis acids such as aluminum chloride, etc. Among them, sulfuric acid and p-toluenesulfonic acid are preferred, and sulfuric acid is particularly preferred.

An amount of the acid catalyst is preferably from 0.01 to 1.0 wt. %, more preferably from 0.05 to 0.5 wt. % based on the weight of the composition for the decomposition of the polysiloxane.

For decomposing the polysiloxane by the method of the present invention, the polysiloxane is simply mixed with the components of the composition for the decomposition of the polysiloxane. For example, the orthoester, the compound having the active hydrogen-containing group and the acid catalyst are mixed to prepare a mixed liquid, and the mixed liquid is contacted with the polysiloxane. This contact can be carried out by any of conventional methods such as coating, dipping, and so on. Alternatively, the polysiloxane is added to the mixed liquid.

Since the reaction of the present invention takes place even at room temperature, it is not necessary to heat the reaction system, which is one of the characteristics of the present invention. Then, the reaction temperature is usually from room temperature to 150° C., preferably from room temperature to 120° C.

EXAMPLES

The present invention will be explained further in detail by the following examples.

Example 1

In a glass vessel, methyl orthoformate (113.56 g, 1.070 mols), methanol (34.97 g, 1.091 mols) and sulfuric acid (0.1 g, 1 mmol) were charged and stirred to prepare a mixed liquid.

In this mixed liquid, a dropper cap made of a vulcanized silicone rubber (4.4 g) was dipped at room temperature for 2 days. When the dropper cap was picked up with forceps, it was broken to pieces. After the dropper cap was kept in the mixed liquid for further three days, a supernatant solution was analyzed by gas chromatography to find that dimethyldimethoxysilane was formed.

Example 2

In the same mixed liquid as used in Example 1, a piece of a silicone rubber sheet of a vulcanized rubber was dipped at room temperature for 2 days. Then, the piece of the silicone rubber sheet was observed to find that its surface was dissolved and changed to a muddy state.

Examples 3 and 4 and Comparative Examples 1, 2 and 3

Methyl orthoformate, methanol, water and sulfuric acid were weighed in amounts shown in Table 1, charged in a glass vessel, and mixed to obtain a mixed liquid.

In this mixed liquid, a dropper cap made of a vulcanized silicone rubber (1.8 g) was dipped at room temperature for 2 days. The results are shown in Table 1.

Example 5

To a mixed liquid of methyl orthoformate (8.41 g, 79.2 mmols), methanol (5.21 g, 0.163 mol) and sulfuric acid (20 mg, 0.20 mmol), methylhydrogenpolysiloxane (KF 99 manufactured by Shinetsu Chemical Co., Ltd.) (10.09 g, 0.157 mol based on the Si—H bonds) was added and stirred at room temperature. After one hour, the mixed liquid was analyzed by gas chromatography to find that 3.88 g (36.5 mmols) of dimethoxymethysilane was formed. Yield: 23% (based on the Si—H bonds).

After 21 hours, the gas chromatographic analysis of the mixed liquid revealed that the amount of dimethoxymethylsilane was increased to 5.28 g (49.7 mmols). Yield: 32% (based on the Si—H bonds).

In the gas chromatography, 1,3-dimethoxy-1,3-dimethyldisiloxane (dimer) was found. Also, peaks corresponding to a trimer and a tetramer were found.

Example 6

In a mixed liquid of methyl orthoformate (7.33 g, 69.1 mmols), methanol (3.98 g, 124 mmols) and sulfuric acid (0.06 g, 0.6 mmol), a powdery ladder polysiloxane (polysilsesquioxane, GLASS-RESIN GR 650) (2.96 g, 44.1 mmols based on Si) was added and dissolved to obtain a homogeneous solution.

After one day at room temperature, no reaction took place. When the solution was analyzed by gas chromatography after 22 days, 3.90 g (28.6 mmols) of methyltrimethoxysilane was formed. Yield: 65% (based on Si). From the gas chromatographic analysis, most of the rest of the product was assumed to be a dimer.

Example 7

In a mixed liquid of methyl orthoformate (4.11 g, 38.7 mmols), methanol (2.41 g, 75.2 mmols) and sulfuric acid (0.04 g, 0.4 mmol), a powdery ladder polysiloxane (polysilsesquioxane, GLASS-RESIN GR 950) (3.20 g, 24.8 mmols based on Si) was added and dissolved to obtain a homogeneous solution.

The mixed liquid was kept standing at room temperature for 22 days. Then, it was analyzed by gas chromatography to find that 21.2 g (10.7 mmols) of phenyltrimethoxysilane was formed. Yield: 43% (based on Si).

Example 8

In a 100 ml two-necked flask equipped with a reflux condenser, a polymethylhydrogensiloxane of the formula:

TABLE 1

|  |  | Ex. 3 | Ex. 4 | C. Ex. 1 | C. Ex. 2 | C. Ex. 3 |
| --- | --- | --- | --- | --- | --- | --- |
| Methyl orthoformate | grams | 21.8 | 21.2 | 21.3 | — | — |
|  | mol | 0.21 | 0.20 | 0.20 | — | — |
| Methanol | grams | 6.4 | — | — | 24.8 | — |
|  | mol | 0.20 | — | — | 0.77 | — |
| Water | grams | — | 1.8 | — | — | 29.8 |
|  | mole | — | 0.10 | — | — | 1.6 |
| Sulfuric acid | milligrams | 23 | 23 | 23 | 23 | 23 |
|  | millimol | 0.23 | 0.23 | 0.23 | 0.23 | 0.23 |
| After dipping at room temperature for 2 days |  | No original shape Complete disintegration | 50% of original shape was disintegrated | No change | No change | No change |

Me$_3$SiO—(MeHSIO)$_{40}$—SiOMe$_3$ (a polymerization degree being an average value) (10.56 g, 0.164 mol based on the Si—H bonds), methyl orthoformate (18.05 g, 0.170 mol), methanol (0.46 g, 0.014 mol) and sulfuric acid (20.5 mg, 0.20 mmol) were mixed at room temperature. As the stirring continued, slight decrease (about 5° C.) of an internal temperature was observed.

After stirring the mixture under the same condition for 6 hours, the reaction mixture was analyzed by gas chromatography and $^1$H-NMR to find that Me(MeO)$_2$SiH was formed in a yield of about 100% based on the Si—H groups in the raw material polysiloxane.

The reaction mixture (22.7 g) was poured in a round bottom 50 ml flask, and rectified through a fractionating tower (an inner diameter of 1.5 cm, a height of 9 cm, packed with metal coils).

First, a temperature of an oil bath was kept at 50° to 75° C., and a fraction having a boiling point of about 30° C. (6.9 g) was collected. Thereafter, since a boiling point started to increase, a collecting vessel was changed, and a colorless liquid having a boiling point of about 50° to 60° C. (11.7 g) was collected. The first fraction contained methyl formate as a main component, and also Me(MeO)$_2$SiH (1.45 g, 0.014 mol). The main fraction contained Me(MeO)$_2$SiH (11.4 g, 0.108 mol). Isolated yield: 81%. Purity: 98%.

Example 9

Using the same apparatus as used in Example 8, polymethylhydrogensiloxane (9.65 g, 0.150 mol based on the Si—H bonds), methyl orthoformate (16.93 g, 0.159 mmol), methanol (10.01 g, 0.312 mol) and sulfuric acid (19 mg, 0.19 mmol) were mixed at room temperature. As the stirring continued, an internal temperature slightly decreased. After stirring the mixture for 2 hours, the reaction mixture was analyzed by gas chromatography to find that Me(MeO)$_2$SiH was formed in a yield of about 100% (based on the Si—H bonds).

This reaction mixture (146.6 g) was rectified through a fractionating tower (an inner diameter of 1.5 cm, a height of 50 cm, packed with glass beads).

First, a temperature of an oil bath was kept at 45° to 70° C., and a first fraction having a boiling point of about 32°–37° C. (43.4 g) was collected. Then, an intermediate fraction having a boiling point of 35°–55° C. (10.1 g) was collected. Thereafter, a main fraction having a boiling point of 59°–61° C. (67.5 g) was collected. The first fraction contained methyl formate as a main component, and the intermediate fraction contains methyl formate and also Me(MeO)$_2$SiH in a weight ratio of about 50:50. The main fraction contained Me(MeO)$_2$SiH (65.4 g, 0.62 mol), Me3SiOMe (1.6 g, 0.015 mol) and methanol (0.1 g, 0.003 mol). Isolated yield: 79%. Purity: 97%.

Comparative Example 4

Using the same apparatus as used in Example 8, polymethylhydrogensiloxane (10.05 g, 0.156 mol), methyl orthoformate (21.9 g, 0.206 mol) and sulfuric acid (41 mg, 0.41 mmol) were mixed. The mixture was stirred at 80° C. for 3 hours, but substantially no Me(MeO)$_2$SiH was formed. Methyl formate was not distilled, and no reaction proceeded.

Examples 13–17 and Comparative Example 5

Hexamethyldisiloxane (61.6 g, 0.38 mol) and methyl orthoformate (40.5 g, 0.38 mol) were mixed to prepare Liquid A. To a part of Liquid A contained in a glass vessel, a compound having an active hydrogen-containing group shown in Table 2 and sulfuric acid as a catalyst were charged to carry out a reaction. After 20 and 100 hours, a yield of Me$_3$SiOMe (based on Si) was measured by $^1$H-NMR. The Yields of Me3SiOMe are shown in Table 2.

TABLE 2

| Component (mol %) | Ex. 13 | Ex. 14 | Ex. 15 | Ex. 16 | Ex. 17 | C. Ex. 5 |
|---|---|---|---|---|---|---|
| Hexamethyldisiloxane | 100 | 100 | 100 | 100 | 100 | 100 |
| Methyl orthoformate | 101 | 101 | 101 | 101 | 101 | 101 |
| Sulfuric acid | 0.6 | 0.6 | 0.6 | 0.6 | 0.6 | 0.6 |
| Water | 5.3 | — | — | — | — | — |
| Methanol | — | 5.1 | — | — | — | — |
| Ethanol | — | — | 5.2 | — | — | — |
| 1-Butanol | — | — | — | 4.8 | — | — |
| Acetic acid | — | — | — | — | 5.2 | — |
| Yield (%) | | | | | | |
| After 20 hrs. | 83 | 52 | 53 | 53 | 35 | 15 |
| After 100 hrs. | 86 | 74 | 80 | 79 | 65 | 17 |

Comparative Example 6

In a 50 ml two-necked flask equipped with a reflux condenser, polymethylhydrogensiloxane (10.1 g, 0.16 mol based on the Si—H bonds), sulfuric acid (20 mg, 0.20 mmols) and methanol (8.7 g, 0.27 mol) were charged and heated on an oil bath kept at 85° C. for 115 minutes while stirring. Thereafter, the Si—H value was 1.01 mmol/g, and 88% of the original Si—H bonds disappeared. A yield of Me(MeO)$_2$SiH according to the gas chromatographic analysis was 2% (based on the Si—H).

Comparative Example 7

In a 200 ml two-necked flask, polymethylhydrogensiloxane (10.0 g, 0.16 mol based on the Si—H bonds), sulfuric acid (70 mg, 0.70 mmols) and methanol (42.2 g, 1.32 mols) were charged and heated on an oil bath kept at 80° C. while stirring, and the evaporated material was passed through a fractionating tower (an inner diameter of 1.5 cm, a height of 9 cm, packed with metal coils) to collect a liquid having a boiling point of 60°–63° C. (34.2 g).

According to the gas chromatographic analysis, the collected liquid contained Me(MeO)$_2$SiH (3.1 g) and rest of methanol. A yield of Me(MeO)$_2$SiH was 19% (based on the Si—H).

Example 10

Using the same apparatus as used in Example 8, polydimethylsiloxane (10.02 g, 0.135 mol based on the Si atoms), methyl orthoformate (15.47 g, 0.146 mol), methanol (0.74 g, 0.023 mol) and sulfuric acid (20 mg, 0.20 mmol) were stirred at room temperature. After stirring for 3 hours, no Me$_2$Si(OMe)$_2$ was formed according to the gas chromatographic analysis. Then, methanol and sulfuric acid were additionally charged till total amounts of methanol and sulfuric acid reached 4.94 g (0.154 mmol) and 60 mg (0.61 mmol), respectively. After stirring the mixture at 50° C. for 8 hours, the reaction mixture was analyzed by gas chromatography to find that Me$_2$Si—(OMe)$_2$ was formed in a yield of 91% (based on the Si atoms).

Example 11

Using the same apparatus as used in Example 8, 1,3,5,7-tetramethylsiloxane (3.03 g, 50.4 mmol based on the Si—H bonds), methyl orthoformate (5.71 g, 53.8 mmol), sulfuric acid (0.02 g, 0.20 mmol) and methanol (0.14 g, 4.4 mmol) were stirred at room temperature for 3 hours. According to the gas chromatographic analysis, Me(MeO)$_2$SiH was formed in a yield of 98% (based on the Si—H bonds).

Example 12

In a 200 ml three-necked flask equipped with a reflux condenser, polymethylhydrogensiloxane (50.0 g, 0.78 mol based on the Si—H bonds), methyl orthoformate (99.2 g, 0.94 mol), methanol (2.50 g, 0.078 mol) and sulfuric acid (0.54 g, 5.5 mmol) were charged and stirred for 180 minutes on an oil bath kept at 50° C.

The reaction mixture was analyzed by gas chromatography to find that Me(MeO)$_2$SiH was formed in a yield of 93% based on the Si—H bonds of the raw material polysiloxane.

EFFECTS OF THE INVENTION

Since the decomposition method of the present invention can be carried out at room temperature, the polysiloxane can be decomposed without the use of an alkali or an acid at high temperature.

Then, this decomposition method is highly effective in re-use of the silicone rubber, removal of the polysiloxane film from the substrate, surface modification of the silicone by partial decomposition, and so on.

In the method for producing the alkoxysilane according to the present invention, since the orthoester and the siloxane or polysiloxane can be reacted in the presence of the alcohol and the acid catalyst under the mild condition of room temperature, undesired by-products are not formed, undesirable side reactions do not substantially take place, and troublesome fractionation of the product is not necessary. Further, the residue does not remain in a large amount.

Since the method of the present invention is a halogenfree method, any halogen compound such as hydrogen chloride or chlorosilane is not formed. Then, the halogen free alkoxysilane is easily produced in a high yield.

In particular, the alkoxysilane having the Si—H bond in the molecule can be readily produced in a high yield.

What is claimed is:

1. A method for decomposing a polysiloxane comprising contacting a polysiloxane with a mixture which comprises an orthoester, a compound having an active hydrogen-containing group and an acid catalyst.

2. The method according to claim 1, wherein said orthoester is a methyl orthoester.

3. The method according to claim 1, wherein said compound having the active hydrogen-containing group is a compound selected from the group consisting of alcohols, water and carboxylic acids.

4. The method according to claim 3, wherein said compound having the active hydrogen-containing group is methanol.

5. The method according to claim 1, wherein said acid catalyst is sulfuric acid.

6. A composition for decomposing a polysiloxane comprising an orthoester, a compound having an active hydrogen-containing group and an acid catalyst.

7. The composition according to claim 6, wherein said orthoester is a methyl orthoester.

8. The composition according to claim 6, wherein said compound having the active hydrogen-containing group is a compound selected from the group consisting of alcohols, water and carboxylic acids.

9. The composition according to claim 8, wherein said compound having the active hydrogen-containing group is methanol.

10. The composition according to claim 6, wherein said acid catalyst is sulfuric acid.

11. A method for producing an alkoxysilane comprising reacting an orthoester with a compound selected from the group consisting of siloxanes and polysiloxanes, in the presence of a compound having an active hydrogen-containing group and an acid catalyst.

12. The method according to claim 11, wherein said siloxane or polysiloxane has a compound having a Si—H bond in a molecule.

13. The method according to claim 11, wherein said orthoester is a methyl orthoester.

14. The method according to claim 11, wherein said compound having the active hydrogen-containing group is a compound which forms an alcohol when it is reacted with the orthoester.

15. The method according to claim 11, wherein said compound having the active hydrogen-containing group is a compound selected from the group consisting of water, carboxylic acids and alcohols.

16. The method according to claim 11, wherein said alkoxysilane has a Si—H bond in a molecule.

17. The method according to claim 11, wherein said alkoxysilane is dimethoxymethylsilane.

* * * * *